United States Patent [19]

Kalopissis et al.

[11] 4,007,228

[45] Feb. 8, 1977

[54] SUBSTITUTED-2-NITRO-PARA-PHENYLENEDIAMINES AND PROCESSES FOR PRODUCING SAME

[75] Inventors: Gregoire Kalopissis, Paris; Andree Bugaut, Boulogne-sur-Seine, both of France

[73] Assignee: L'Oreal, Paris, France

[22] Filed: Sept. 2, 1970

[21] Appl. No.: 69,116

Related U.S. Application Data

[62] Division of Ser. No. 508,568, Nov. 18, 1965, Pat. No. 3,555,584.

[30] Foreign Application Priority Data

Nov. 19, 1964 Luxembourg .......................... 47386

[52] U.S. Cl. ............................................... 260/573
[51] Int. Cl.$^2$ ......................................... C07C 91/06
[58] Field of Search ..................................... 260/573

[56] References Cited

UNITED STATES PATENTS

| | | | |
|---|---|---|---|
| 2,750,326 | 6/1956 | Eckardt | 260/573 X |
| 3,168,442 | 2/1965 | Brunner et al. | 260/573 X |
| 3,194,838 | 7/1965 | Ross et al. | 260/573 |

FOREIGN PATENTS OR APPLICATIONS

| | | | |
|---|---|---|---|
| 1,137,922 | 1/1957 | France | 8/10.1 |
| 13,956 | 4/1905 | United Kingdom | 260/573 |

OTHER PUBLICATIONS

Vogel, Arthur I., Practical Organic Chemistry, Third Edition, pp. 122–133, John Wiley & Sons, Inc. New York, New York.

*Primary Examiner*—Charles F. Warren
*Attorney, Agent, or Firm*—Brisebois & Kruger

[57] ABSTRACT

The compound (2'-hydroxyethyl)-1-amino-2-nitro-(2'-hydroxyethyl)-4-methylamino benzene which can be used to dye live human hair.

3 Claims, No Drawings

SUBSTITUTED-2-NITRO-PARAPHENYLENEDIAMINES AND PROCESSES FOR PRODUCING SAME

SUMMARY OF THE INVENTION

This application is a division of application Ser. No. 508,568, filed Nov. 18, 1965 which is now U.S. Pat. No. 3,555,584.

Substituted nitroparaphenylenediamines are well known active ingredients of hair dyes, and particularly of dyes for human hair. Among the different substituents proposed with a view to obtaining deeper shades than those obtained with nitroparaphenylenediamine itself are the alkyl groups and the hydroxyalkyl groups. In particular it has been suggested that the trihydroxyalkylated derivatives of nitroparaphenylenediamine be used, and especially those trihydroxyethylated derivatives which have a hydroxyethyl radical on the amino group in the ortho position of the nitro group and two hydroxyethyl radicals on the amino group in the meta position of the nitro group.

However, it is very difficult to obtain a trihydroxyethylated derivative of the type in question from nitroparaphenylenediamine, by reaction with a halohydrine, for example, in a commerically adequate percentage of yield, without painstaking purification, because the substitution of the hydroxyethylated groups for the hydrogens of the amine functions leads in practice, not to a pure trihydroxyethylated product, but to a mixture of mono-, di-, and trisubstituted products, each having its own coloring power, said mixture often comprising also tarray impurities.

Under the operating conditions under which this substitution is carried out, the proportions in such a mixture vary, and the results obtained by using such a mixture cannot be consistently reproduced.

The object of the present invention is to provide a new dye and new coloring compositions based on said new dye.

The said new dye is:
(2'-hydroxyethyl)-1-amino-2-nitro-(2'-hydroxyethyl)-4-methylamino benzene.

The invention also relates to two processes of preparing this new dye.

The first method described below in Example A results in a mixture comprising a mixture of the product of this invention which is di-hydroxyethylated in 1-4 position and a product which is mono-hydroxyethylated in position 4, while the amine function which occupies position 1 in the dye according to the invention remains unsubstituted. The process of separating the reaction products obtained by this process is long and difficult, but it is highly important that this separation be made, because the presence of the mono-hydroxyethylated product has a substantial effect on the shade produced and if a mixture of both these reaction products is used, the fact that the proportion between the products is dependent on the reaction conditions makes it impossible to obtain a perfectly reproducible shade. The use of this first method of preparation is therefore accompanied by definite inconveniences. This process has, however, been described, since the dye according to the invention may be produced in this manner. Said process is essentially characterized by the fact that a glycol halohydrine is reacted with 1-amino-2-nitro-4-methylamino benzene, (a composition heretofore known in itself) and that the resulting mono and di-hydroxyethylated products are then separated.

The second process of preparing the dye according to the invention, which is described in Example B, makes it possible to efficiently substitute a hydroxyethyl radical for a hydrogen of the amine function in the ortho position of the nitro group. This process is essentially characterized by the fact that 1-amino-2-nitro-4-methylacetamino-benzene is reacted with chloroethyl-chloroformiate to block the position occupied by one of the hydrogen atoms initially bonded to the nitrogen atom in position 1 and the fact that concentrated hydrochloric acid is used to deacetylate the product thereby obtained, after which potash is added to cause hydroxyethylation in position 1 and a glycol halohydrine is introduced to cause hydroxyethylation in position 4.

It has been found that the use of (2'-hydroxyethyl)-1-amino-2-nitro-(2'-hydroxyethyl-4-methylamino-benzene produces perfectly uniform deep violet shades on live human hair.

Moreover, this dye has an excellent affinity for the keratinic fibers of human hair and the colors produced thereby are particularly resistant to shampooing and have no coloring effect on the scalp.

The hair dyeing compositions containing this dye are simple aqueous solutions having preferably an alkaline pH. The pH of these solutions is generally between 7 and 10 and preferably between 8 and 9.5. Ammonia, or any organic base such as an alkylamine, an alkanolamine, or a heterocyclic amine may be used to adjust the pH.

Moreover, the dyeing solutions according to the invention may include various conventional ingredients such as, for example, organic solvents, detergents, and lacquers, that are suitable for use on live human hair.

The dye of this invention may also be mixed with other dyes such as nitrated dyes, azo dyes, anthroquinone dyes, or any other type of dye conventionally used to dye human hair to produce a variety of different hair colors.

In use, these dyes do not require the employment of an oxidizing agent. The time in contact with the hair may vary within broad limits but falls preferably between 5 and 30 minutes. The temperature of application may also be varied, but the dye is preferably used at room temperature. The concentration of the dye of this invention in the dyeing solutions may also be varied, but this concentration is preferably between 0.1 and 3%.

The processes of preparing the dye of this invention will now be described in Examples A and B. It will be recalled that the process of Example A is more difficult to carry out than the process of Example B.

EXAMPLE A

First process of preparing (2'-hydroxyethyl)-1-amino-2-nitro-(2'-hydroxyethyl)-4-methylamino benzene.

A mixture containing 0.05 mols (8.35 g) of 1-amino-2-nitro-4-methylamino benzene, 65 cm$^3$ of water and 9.6 g of calcium carbonate is heated to reflux. 0.2 mols (14 cm$^3$) of glycol bromohydrine is added little by little and kept at reflux for an hour and a half. After cooling the mixture is acidified, using 12 cm$^3$ of hydrochloric acid to destroy the excess calcium carbonate, and brought to an alkaline pH, using ammonia. Since it is difficult to substitute a hydrogen of the amine function in the ortho position of the nitro group, this process always yields a mixture of the product sought and 1-amino-2-nitro-(2'-hydroxyethyl)-4-methylamino benzene.

These two products are separated in the following manner: The resulting mixture is drained to yield 4.5 g of a product which melts at 110° C and consists almost entirely of the monohydroxyethylated derivative. After several recrystallizations, 3 g of pure 1-amino-2-nitro-(2'-hydroxyethyl)-4-methylamino benzene, which melts at 114° C, is obtained. The isomer (2'-hydroxyethyl)-1-amino-2-nitro-4-methylamino benzene melts at 120° C and the mixture of these two isomers melts at 100° C.

|  | Calculated | Found |
|---|---|---|
| C % | 51.18 | 50.89 – 50.98 |
| H % | 6.16 | 6.16 – 6.43 |
| N % | 19.90 | 20.21 – 20.23 |

This mono-hydroxyethylated product may also be used as a hair dye.

In order to obtain the di-hydroxyethylated product after the above draining step, the mother liquid is extracted, using methyl-isobutyl-ketone and vacuum concentrated. After cooling, the yield is 3.8 g of a raw product which melts at 80° C and the major part of which consists of the dihydroxyethylated derivative. After recrystallization in ethyl acetate, 2.7 g of (2'-hydroxyethyl)-amino-2-nitro-(2'-hydroxyethyl)-4-methylamino benzene which melts at 99° C is obtained by drying.

EXAMPLE B

Second method of preparing (2'-hydroxyethyl)-1-amino-2-nitro-(2'-hydroxyethyl)-4-methylamino benzene.

This process is carried out in four steps:

a. Preparation of the $\beta$-chloroethylic ester of (2-nitro-4-methylacetamino) phenylcarbamic acid.

0.17 mols (35 g) of 1-amino-2-nitro-4-methylacetamino benzene are dissolved in 200 cm³ of methyl-isobutyl-ketone. After adding 12 g of calcium carbonate 0.2 mols (28.8 g) of chlorethyl-chloroformiate is introduced little by little, at reflux and while stirring. Reflux is maintained for three hours. The product is filtered while boiling to eliminate mineral salts. The solvent is driven off under vacuum and the oily residue is treated with ether to crystallize it. Drying yields 44 g of the $\beta$ chloroethylic ester of (2-nitro-4-methyl-acetamino-phenylcarbamic acid, which melts at 83° C.

|  | Calculated | Found |
|---|---|---|
| C % | 45.64 | 45.46 – 45.55 |
| H % | 4.43 | 4.62 – 4.50 |
| N % | 13.31 | 13.16 – 13.32 | b. Preparation of the $\beta$ chloroethylic ester of (2-nitro-4-methylamino)-phenylcarbamic acid.

0.232 mols (73.3 g) of the $\beta$ chloroethylic ester of (2-nitro-4-methylacetamino) phenylcarbamic acid are introduced into a mixture containing 79 cm³ of concentrated hydrochloric acid, 158 cm³ of water and 43 cm³ of acetic acid. This is brought to reflux for an hour, cooled in a mixture of ice and salt and yields 58 g of crystallized hydrochlorate on drying. The hydrochlorate is dissolved in water, brought to an alkyline pH with ammonia, and 49 g of the $\beta$ chloroethylic ester of (2-nitro-4-methylamino)-phenylcarbamic acid is obtained on drying. This ester melts at 90° C.

|  | Calculated | Found |
|---|---|---|
| C % | 43.87 | 44.13 – 44.01 |
| H % | 4.38 | 4.56 – 4.48 |
| N % | 15.35 | 15.63 – 15.05 | c. Preparation of (2'-hydroxyethyl)-1-amino-2-nitro-4-methylamino benzene.

0.056 mols (15.5 g) of the $\beta$ chloroethylic ester of (2-nitro-4-methylamino)-phenylcarbamic acid is heated to reflux for two hours in 140 cm³ of an alcoholic potash solution containing 110 g of potash per liter. This is cooled, emptied into a liter of ice water and dried to yield 9.5 g of (2'-hydroxyethyl)-1-amino-2-nitro-4-methylamino benzene which melts at 120° C.

|  | Calculated | Found |
|---|---|---|
| C% | 51.18 | 51.39 – 51.31 |
| H% | 6.16 | 6.39 – 6.30 |
| N% | 22.74 | 22.54 – 22.62 | d. Preparation of (2'-hydroxyethyl)-1-amino-2-nitro-(2'-hydroxyethyl)-4-methylamino benzene.

The substitution of a hydrogen of the amine function in the meta position of the nitro group is easily accomplished in the following manner. A mixture of 0.086 mols (18.1 g) of (2'-hydroxyethyl)-1-amino-2-nitro-4-methylamino benzene with 110 cm³ of water and 6.25 g of calcium carbonate is brought to reflux. 0.124 mols (8.75 cm³) of glycol bromohydrine is then introduced drop by drop, while stirring. Reflux is maintained for an hour and a half and then the reaction mixture is cooled and acidified with hydrochloric acid. The crystallized hydrochlorate is then dried, redissolved in water, and brought to an alkaline pH by adding ammonia. Drying yields 16 g of (2'-hyroxyethyl)-1-amino-2-nitro-(2'-hydroxyethyl)-4-methylamino benzene which melts at 99° C.

|  | Calculated | Found |
|---|---|---|
| C% | 51.76 | 51.64 – 51.90 |
| H% | 6.66 | 6.83 – 6.85 |
| N% | 16.47 | 16.34 – 16.57 |

Several examples showing how the dye according to the invention may be used to color the hair will now be given.

EXAMPLE 1

The following solution is prepared:

| | |
|---|---|
| (2'-hydroxyethyl)-1-amino-2-nitro-(2'-hydroxyethyl)-4-methylamino benzene | 0.5 g. |
| Lauric alcohol oxyethylenated with 20 molecules | |

| | |
|---|---|
| of ethylene oxide | 5 g. |
| Ammonia q.s.p. | pH 9 |
| Water q.s.p. | 100 |

This solution is applied to completely white hair and left for ten minutes. The hair is then rinsed, washed, and dried, and the shade obtained is mauve.

EXAMPLE 2

The following solution is prepared:

| | |
|---|---|
| (2'-hydroxyethyl)-1-amino-2-nitro-(2'-hydroxyethyl)-4-methylamino benzene | 0.7 g. |
| 1-hydroxy-2-amino-5-nitro-benzene | 0.12 g. |
| Sodium salt of N-(N',N'-diethylaminopropyl)-N²-fatty alkyl-asparagine having the formula: | |

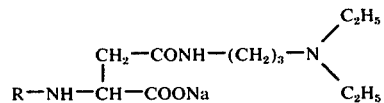

| | |
|---|---|
| in which R is the alkyl residue of the fatty acids of copra | 1 g. |
| 50% solution of sodium salt of N(N',N'-diethylaminopropyl)-N₂-fatty alkyl-asparagine having the formula: | |

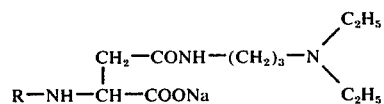

| | |
|---|---|
| in which R represents the alkyl residue of the fatty acids of tallow | 1 g. |
| Lauric alcohol oxyethylenated with 20 molecules of ethylene oxide | 3 g. |
| Diethanolamide of copra | 2 g. |
| Ammonia q.s.p. | pH 9 |
| Water q.s.p. | 100 g. |

This solution is applied to 90% white hair for 20 minutes. The hair is then rinsed and washed. After drying, a clear chestnut is obtained.

EXAMPLE 3

The following solution is prepared:

| | |
|---|---|
| (2'-hydroxyethyl)-1-amino-2-nitro-(2'-hydroxyethyl)-4-methylamino benzene | 0.6 g. |
| 1-hydroxy-2-amino-5-nitro benzene | 0.1 g. |
| Nitroparaphenylenediamine | 0.01 g. |
| 1-amino-2-nitro-4-methylamino benzene | 0.07 g. |
| Sodium salt of N(N',N'-diethylaminopropyl)-N²-alkyl-asparagin having the formula: | |

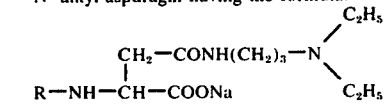

| | |
|---|---|
| in which R is the alkyl residue of the fatty acids of copra | 1 g. |
| 50% solution of the sodium salt of N(N',N'-diethylaminopropyl)-N₂-alkyl-asparagine having the formula: | |

$$CH_2-CONH(CH_2)_3-N\begin{matrix}C_2H_5\\ \\C_2H_5\end{matrix}$$
$$R-NH-CH-COONa$$

| | |
|---|---|
| in which R represents the alkyl residue of the fatty acids of tallow | 1 g. |
| Lauric alcohol oxyethylenated with 20 molecules of ethylene oxide | 3 g. |
| Diethanolamide of copra | 2 g. |
| Ammonia q.s.p. | pH 9 |
| Water q.s.p. | 100 g. |

This solution is applied to 90% white hair for 20 minutes. The hair is then rinsed and washed. After drying, a reddish chestnut is obtained.

What is claimed is:

1. (2'-hydroxyethyl)-1-amino-2-nitro-(2'-hydroxyethyl)-4-methylamino benzene.

2. The method of making a high purity (2'-hydroxyethyl)-1-amino-2-nitro-(2'-hydroxyethyl)-4-methylamino benzene of claim 1 which comprises the steps of reacting 1-amino-2-nitro-4-methyl-acetamino benzene with reactive amounts of chloroethylchloroformiate to obtain the chloroethylic ester of (-2-nitro-4-methylacetamino) phenylcarbamic acid, deacetylizing the resulting product with deacetylating amounts of concentrated hydrochloric acid to obtain the chloroethylic ester of (2-nitro-4-methylamino)-phenylcarbamic acid, reacting this product with a potash solution to obtain (2'-hydroxyethyl)-1-amino-2-nitro-4-methylamino benzene, and then reacting this product with glycol halohydrine to produce (2'hydroxyethyl)-1-amino-2-nitro-(2'hydroxyethyl)-4-methylamino benzene.

3. The method of claim 2 in which said halohydrine is bromohydrine.

* * * * *